United States Patent [19]

Smith, III et al.

[11] 4,408,059

[45] Oct. 4, 1983

[54] SPIROKETALS USEFUL AS INTERMEDIATES IN THE SYNTHESIS OF MILBEMYCIN AND AVERMECTIN MACROLIDES

[75] Inventors: Amos B. Smith, III, Merion, Pa.; Steven R. Schow, Wilmington, Del.

[73] Assignee: University Patents, Inc., Norwalk, Conn.

[21] Appl. No.: 327,641

[22] Filed: Dec. 4, 1981

[51] Int. Cl.³ .................. C07D 309/06; C07D 493/22; C07H 17/08; C07C 65/00

[52] U.S. Cl. ..................... 549/214; 536/7.1; 549/264; 549/343; 549/414; 549/425; 560/18; 560/46; 560/65; 560/67; 560/64; 560/70; 560/72; 562/432; 562/453; 562/473; 562/474; 562/475; 562/476; 548/240

[58] Field of Search ........................ 549/343, 264

[56] References Cited

U.S. PATENT DOCUMENTS

| | | | |
|---|---|---|---|
| 3,099,662 | 7/1963 | Wassan et al. | 549/343 |
| 3,950,360 | 4/1976 | Aoki et al. | 549/264 |
| 4,093,629 | 6/1978 | Fisher | 549/264 |
| 4,171,314 | 10/1979 | Chabala et al. | 549/264 |
| 4,200,581 | 4/1980 | Fisher et al. | 549/264 |

OTHER PUBLICATIONS

Smith, III et al., Chem. Abstract, 97, 92011h (1982).
Albers-Schönberg et al., JACS. 103, 4216 (1981).

*Primary Examiner*—Nicky Chan
*Attorney, Agent, or Firm*—George M. Yahwak

[57] ABSTRACT

Milbemycin and avermectin macrolides are synthesized by the cyclized linking of separately synthesized northern and southern hemisphere intermediates. The northern hemisphere intermediate is a spiroketal alkenyl aldehyde, and the southern hemisphere intermediate is an aryl alkenyl phosphine oxide anion.

6 Claims, No Drawings

SPIROKETALS USEFUL AS INTERMEDIATES IN THE SYNTHESIS OF MILBEMYCIN AND AVERMECTIN MACROLIDES

BACKGROUND OF THE INVENTION

The invention described herein was made in the course of work carried out under a grant or award from the Department of Health and Human Services.

This invention relates to a total synthetic route for the preparation of milbemycin and avermectin macrolides, and to novel compounds employed as intermediates in such synthesis.

The milbemycins and avermectins are a series of macrolide antibiotics known to have closely related chemical structures and to exhibit highly potent anthelmintic, insecticidal, ectoparasiticidal and acaricidal activity. The known preparative procedures for these macrolides have all employed fermentation techniques, the avermectins being isolated from the fermentation broth of *Streptomyces avermitilis*, and the milbemycins being isolated from the fermentation broth of a strain of Streptomyces identified as the B-41-146 strain.

The fermentation and isolation procedures, and the chemical structures and properties of the milbemycins and avermectins, are more fully described in U.S. Pat. Nos. 3,950,360; 3,984,564; 3,992,551; 4,093,629; and 4,144,352; Tetrahedron Letters, No. 10, pages 711–714, 1975; Journal of Antibiotics, Volume 29, No. 6, June, 1976, pages 76-35 to 76-42 and pages 76-14 to 76-16; Antimicrobial Agents and Chemotherapy, Volume 15, No. 3, March, 1979, pages 361–367; and Journal of Antibiotics, Volume 33, No. 10, October, 1980, pages 1120–1127.

SUMMARY OF THE INVENTION

It is, accordingly, a primary object of the present invention to provide a preparative procedure for the total synthesis of milbemycin and avermectin macrolides.

Another object of the invention is to provide novel compounds useful as intermediates in the total synthesis of milbemycin and avermectin macrolides.

The above and other objects are achieved in accordance with the present invention by separately synthesizing a northern hemisphere intermediate and a southern hemisphere intermediate, and thereafter effecting a cyclized linking of the two intermediates. The northern hemisphere intermediate is a spiroketal alkenyl aldehyde (Formulas XII and XII-A in the following reaction scheme), and the southern hemisphere intermediate is an aryl alkenyl phosphine oxide anion (Formulas XX and XX-A in the following reaction scheme).

The synthesis procedure of the present invention is summarized in the following reaction scheme.

(A) Synthesis of Northern Hemisphere Intermediate

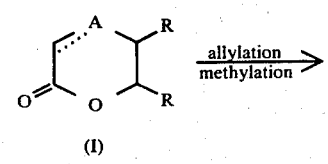

(I)

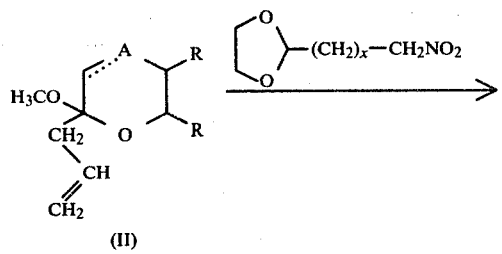

(II)

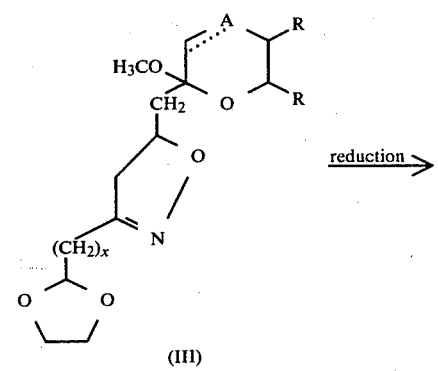

(III)

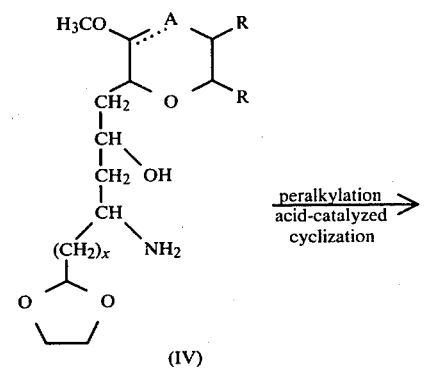

(IV)

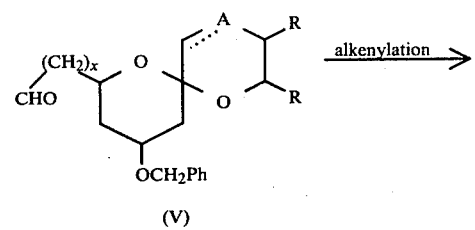

(V)

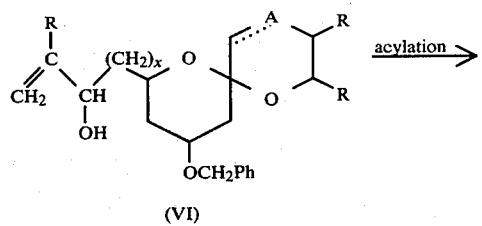

(VI)

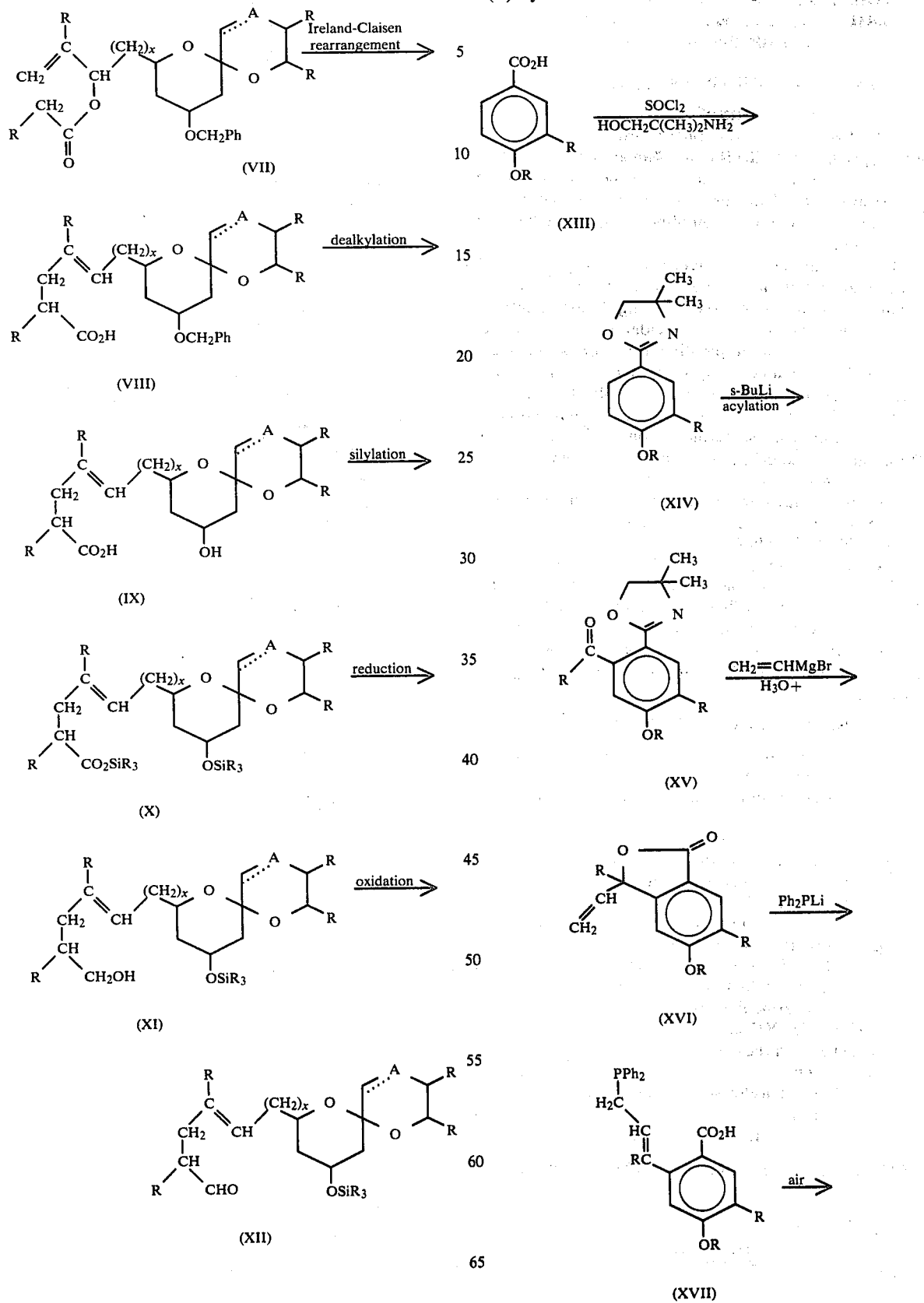

-continued

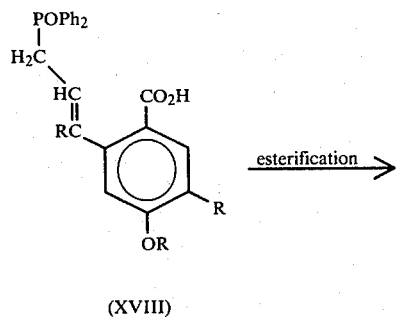

(XVIII)

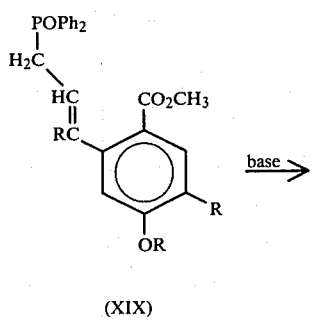

(XIX)

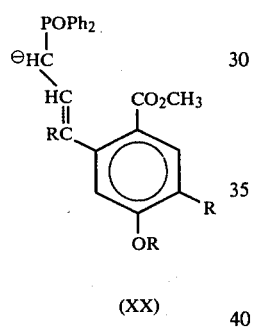

(XX)

(C) Linking of Northern and Southern Hemisphere Intermediates

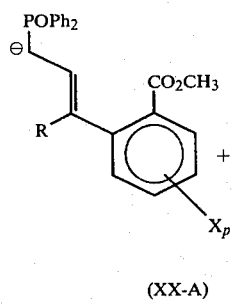

(XX-A)

+

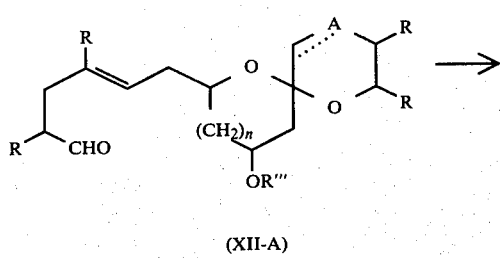

(XII-A)

-continued

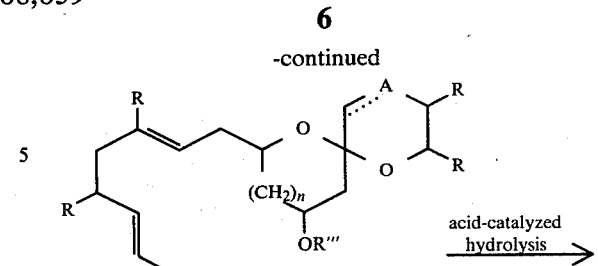

(XXI)

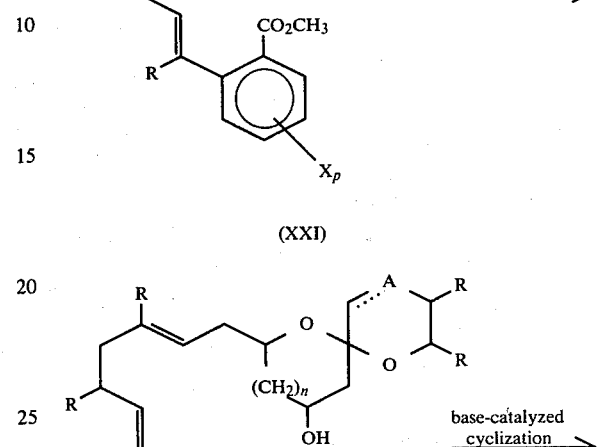

(XXII)

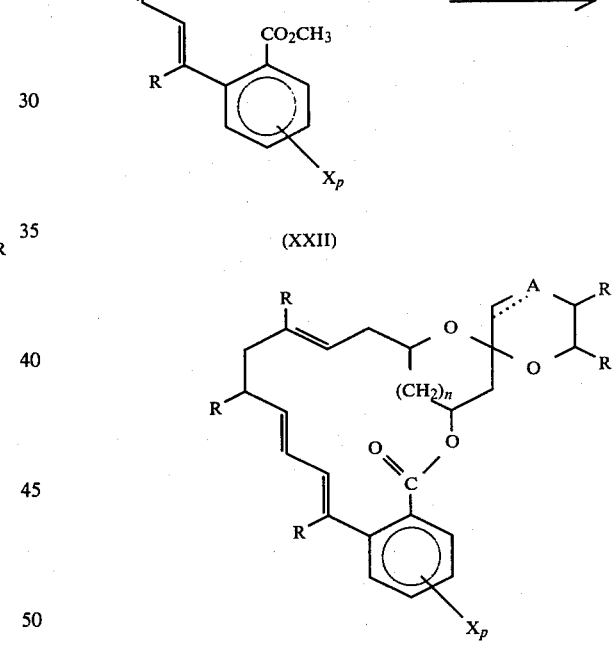

(XXIII)

In the various formulas set forth in the above reaction scheme, A is $(CH_2)_n$ or $(CH_2)_m CH$; n is an integer of from 0 to 3; m is an integer of from 0 to 2; x is an integer of from 1 to 20; R is H, alkyl, or aryl; R''' is a protecting group (e.g., $SiR_3$); Ph is phenyl; X is a substituent selected from the group consisting of alkyl, aryl, aralkyl, OR, SR, $NR_2$, halogen, $CF_3$, and $CCl_3$; p is an integer of from 0 to 4; and when p is greater than 1, the X's may be the same or different.

The present invention also encompasses novel compounds obtained as, or readily derivable from, the various intermediates prepared during the course of the above-described reaction scheme. Such novel compounds include the spiroketal compounds of Formula XXIV, and the aryl alkenyl phosphine oxides of Formula XXV.

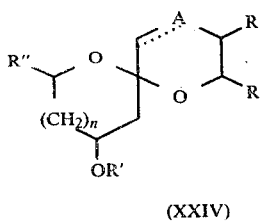

(XXIV)

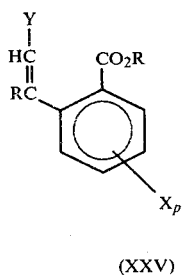

(XXV)

In Formulas XXIV and XXV, A, R, X, n and p are as defined above; R' is H, alkyl, aryl, aralkyl, COR, or $SiR_3$; R" is H, OR, $CH_2OR$, $(CH_2)_xZ$, $(CH_2)_x$—CH($OZ'$)—CR=$CH_2$, or $(CH_2)_x$—CH=CR—$CH_2$—CHR—Z; Z is H, CHO, $CH_2OR$, $CO_2R$, or $CO_2SiR_3$; Z' is H or $COCH_2R$; x is as defined above; Y is $CH_2$—$POPh_2$ or $\ominus CH$—$POPh_2$; and Ph is phenyl.

In the above definitions of R, R' and X, alkyl is preferably lower alkyl; aryl includes, for example, phenyl, biphenyl and naphthyl, and may be either unsubstituted or substituted, e.g., with the various substituents encompassed by the definition of X; and aralkyl is preferably benzyl, and may be either unsubstituted or substituted in the same manner as described above for aryl.

The novel compounds of Formulas XXIV and XXV have utility as intermediates in the total synthesis of milbemycin and avermectin macrolides in accordance with the above-described reaction scheme. It is also believed that a number of these novel compounds, particularly the spiroketal compounds of Formula XXIV, include the chemical structure responsible for the biological activity of the various milbemycin and avermectin macrolides, and hence may themselves have utility as anthelmintic, insecticidal, ectoparasiticidal or acaricidal agents significantly simplified in chemical structure in comparison with the prior art compounds exhibiting similar biological activity.

DESCRIPTION OF PREFERRED EMBODIMENTS

The invention is described in further detail with reference to the reaction scheme set forth above.

(A) Synthesis of Northern Hemisphere Intermediate

The starting material in the synthesis of the northern hemisphere intermediate is the lactone of Formula I. The lactone is converted to a mixed alcohol ketal of Formula II by reaction with an allyl organometallic reagent, such as allyl magnesium chloride, and reacting the resulting hemiketal with a methylating agent, such as methyl orthoformate, in the presence of cerium chloride or other acid catalyst. The ketal of Formula II is then reacted with a 2-nitroalkyl-1,3-dioxolane, such as 2-(β-nitroethyl)-1,3-dioxolane, in the presence of a dehydrating agent such as phenylisocyanate, to form by cycloaddition the isoxazole of Formula III. Reduction of the isoxazole with, for example, $LiAlH_4$, provides the aminol of Formula IV.

Peralkylation of the aminol of Formula IV with KH/benzyl iodide and methyl iodide, followed by acid-catalyzed cyclization, yields the spiroketal aldehyde of Formula V. Alkenylation of the spiroketal aldehyde of Formula V with an organometallic reagent, such as isopropenyl magnesium bromide, provides the spiroketal alkenyl alcohol of Formula VI, wherein the CHO group has been converted to CH(OH)—CR=$CH_2$. Acylation with, for example, propionyl chloride, gives the corresponding ester of Formula VII.

Rearrangement of the spiroketal ester of Formula VII to the spiroketal alkenyl acid of Formula VIII, is effected by means of the Ireland-Claisen rearrangement which is described in detail in the Journal of the American Chemical Society, Volume 98, page 2868 (1976), incorporated herein by reference. In carrying out such rearrangement, the ester is mixed with $KN[Si(CH_3)_3]_2$, $(CH_3)_3SiCl$ and hexamethylphosphoramide, and reacted at about 50° C., and thereafter, following cooling, treated with $Bu_4NF$.

The spiroketal alkenyl acid of Formula VIII, is then dealkylated, for example, with lithium in liquid ammonia, so as to convert the benzyl ether group to an alcohol (Formula IX), and thereafter subjected to silylation with, for example, t-$BuMe_2SiCl$ and imidazole, to form the silyl ester-silyl ether derivative of Formula X. This derivative is then subjected to reduction with, for example, $LiAlH_4$, to convert the silyl ester group to an alcohol group. The resulting spiroketal alkenyl alcohol of Formula XI is then subjected to oxidation, for example, with preformed Collins reagent (pyridine-$CrO_3$ in $CH_2Cl_2$), to convert it to the O-protected spiroketal alkenyl aldehyde of Formula XII.

By suitable modifications appararent to those skilled in the art in the choice of reagents employed, the above-described procedure for synthesizing the northern hemisphere intermediate may be carried out so as to provide the intermediate with the structural variations encompassed in Formula XII-A, i.e., variations in the O-protecting group and in the number of carbon atoms in the spiroketal moiety.

(B) Synthesis of Southern Hemisphere Intermediate

The starting material used in the synthesis of the southern hemisphere intermediate is a benzoic acid derivative of the Formula XIII. The benzoic acid derivative is reacted with thionyl chloride and 2-methyl-2-aminopropanol to convert it to the aryloxazoline of Formula XIV. The aryloxazoline is converted to the ortho ketone of Formula XV by ortho metalation with s-BuLi, followed by acylation, for example, with acetic anhydride. Vinyl organometallic addition to the ketone, followed by acid-catalyzed hydrolysis, gives the lactone of Formula XVI.

The lactone is then reacted with lithium diphenylphosphide to form an aryl alkenyl phosphine of Formula XVII, which is then converted to the corresponding aryl alkenyl phosphine oxide of Formula XVIII by oxidation, for example, by bubbling air through a solution of the phosphine. The phosphine oxide is then subjected to esterification, for example, with diazomethane, to convert its carboxyl group to the methyl ester. The esterified phosphine oxide of Formula XIX is then subjected to base treatment to convert it to the aryl alkenyl phosphine oxide anion of Formula XX, which constitutes the southern hemisphere intermediate.

By suitable modifications apparent to those skilled in the art in the choice of reagents employed and/or by subsequent derivatization, the above-described procedure for synthesizing the southern hemisphere intermediate may be carried out so as to provide the structural modifications encompassed by Formula XX-A, i.e., variations in the substituents on the aryl ring.

(C) Linking of Northern and Southern Hemisphere Intermediates

The O-protected spiroketal alkenyl aldehyde of Formula XII-A, constituting the northern hemisphere intermediate, and the aryl alkenyl phosphine oxide anion of Formula XX-A, constituting the southern hemisphere intermediate, are reacted together in basic solution, to form the diene-linked O-protected intermediate of Formula XXI. The linked intermediate is then deprotected by acid-catalyzed hydrolysis to form the alcohol of Formula XXII. Upon treatment with base, the deprotected intermediate becomes cyclized by reaction between the OH group on the spiroketal moiety and the $CO_2CH_3$ group on the aryl moiety, to form the spiroketal macrolide of Formula XXIII.

The invention is further illustrated by way of the following example.

Example

This example illustrates the synthesis of a spiroketal macrolide encompassed by Formula XXIII, by separate synthesis and subsequent cyclized linking of a northern hemisphere intermediate of Formula XII and a southern hemisphere intermediate of Formula XX, with reference to the reaction scheme set forth above, wherein A is $CH_2$, n is 1, x is 1, and all R's are methyl unless otherwise indicated.

(A) Synthesis of Northern Hemisphere Intermediate (1) Conversion of I to II

To 5.0 g (39 mmole) of lactone I in 100 ml of THF@ −78° C. was added 32 ml (38.4 mmol) of 1.2 molar allyl magnesium chloride/THF solution. Addition required ca. 4 minutes. The reaction mixture was stirred at −78° C. for 3 hours, then quenched with saturated $NH_4Cl$ and extracted with ether. The ether extracts were combined, washed with brine, and dried with $MgSO_4$. The solvent was removed in vacuo and the remaining residue was taken up in 25 ml methyl orthoformate. The resulting solution was then treated with ca 200 mg $CeCl_3.XH_2O$ for 16 hours. The methylorthoformate was removed in vacuo at room temperature. The cerium salts were precipitated with pentane. Filtration and removal of the pentane in vacuo yielded crude ketal II. Flash chromat. (Hex:ethyl acetate 20:1; 10:1) gave 5.0 g (71%) of desired product as a pale yellow oil. Flash distillation (~2 torr; 60°-70° C.) gave a water white liquid.

(2) Conversion of II to III

A solution of 1.0 g (5.4 mmole) ketal II; 1.0 g (6.8 mmole) 2-(β-nitroethyl)-1,3-dioxolane; 2.4 g (20.1 mmole) phenylisocyanate and a trace of triethylamine (TEA) in 20 ml of benzene was stirred overnight at room temperature. The solids were removed and washed with benzene. The solvent was removed in vacuo and the residue was flash chromat. (Hex:ethylacetate-10:1; 5:1; 1:1). The reaction mixture yielded 1.56 g (92%) of isoxazole III.

(3) Conversion of III to IV to V

A solution of 5.47 g (18.2 mmole) of isoxazole III in 20 ml of ether was added dropwise to 3.07 (78.9 mmole) $LiAlH_4$ in 100 ml of ether. Upon completion of addition, the reaction mixture was refluxed for 5 hours, then stirred overnight at room temperature. The reaction was quenched with $Na_2SO_4.H_2O$, then filtered. The ether was removed in vacuo to yield 5.4 g crude aminol IV (94%). To a slurry of 108 g (270 mmol) KH in 150 ml THF was added simultaneously 6.7 g (30.7 mmole) benzyl iodide and 4.9 g (15.5 mmole) of the crude aminol IV in 10 ml THF. The slurry was stirred at room temperature for 3 hours, then 20 ml (320 mmole) of methyl iodide was added and stirring continued for 2 days. As much of the remaining methyl iodide as possible was removed in a stream of argon. The residue was quenched with aqueous THF, then made acidic with excess tosic acid. The solution was then diluted with THF and water until a clear solution resulted. The solution was stirred at room temprature for 8 hours. The crude spiroketal aldehyde V was extracted with ether. The ether extracts were combined and dried over $MgSO_4$. The solvent was removed in vacuo and the resulting residue was flash chromat. (variable gradient-Hex:ethylacetate). The spiroketal aldehyde V was crystallized from hexane to yield 1.4 g (27%) mp: 58°-59° C.

(4) Conversion of V to VI to VII

To a solution 8 ml of 0.63 molar isopropenyl magnesium bromide in ether (5.0 mmole) at −20° C. was added 1.1 g (3.3 mmole) spiroketal aldehyde V in 10 ml ether. The reaction mixture was warmed to room temperature and stirred for 1 hour. The reaction was quenched with saturated $NH_4Cl$ solution and extracted with ether. The ether was removed in vacuo, then the residue was redissolved in 25 ml of $CH_2Cl_2$. The solution was cooled to 0° C. and treated with 3 ml TEA and trace DMAP followed by 2 ml propionyl chloride. The solution was stirred for 1 hour at 0° C. then quenched with saturated $NaHCO_3$ and extracted with ether. The ether extract was back washed with brine and dried with $MgSO_4$. In vacuo removal of the ether followed by flash chromatog. (variable gradient Hex. ethyl acetate) of the residue gave 0.92 g (65%) of a mixture of diastereomers. The diastereomers could be separated by medium pressure LC (variable gradient Hex:ethyl acetate).

(5) Conversion of VII to VIII

To a solution of 1.6 ml of 0.82 molar $KN[Si(CH_3)_3]_2$/THF (1.31 mmole) in 2 ml of THF at −78° C. was added 40 mg (0.16 mmole) of spiroketal ester VII in 0.5 ml THF. The reaction was stirred for 7 min., then 0.25 ml of hexamethylphosphoramide was added. The solution was stirred for 5 min., then 0.3 ml of 75% $(CH_3)_3SiCl.TEA$ solution (1.77 mmol) was added. The reaction mixture was warmed to 56° C. over ~1.5 hours. The solution was then cooled and diluted with excess 10% HCl. The mixture extracted with ether. The ether extracts were back washed with water followed by brine. The ether was removed in vacuo. The residue was then taken up in wet THF and treated with 1 ml of 1 molar $Bu_4NF$/THF solution for 1 hour. The solvent was then removed in vacuo and the crude spiroketal alkenyl acid VIII was purified by flash chromatography (variable gradient Hex:ethyl acetate). The starting material was recovered (31.2 mg) and 36.4 mg (52%) of desired acid VIII was isolated.

(6) Conversion of VIII to IX to X to XI to XII

A solution of 36.4 mg (0.985 mmole) of spiroketal alkenyl acid VIII in 0.5 ml of THF was added to excess lithium (~25 mg) in 15 ml of liquid ammonia. The reaction was stirred for 20 minutes then quenched with $NH_4Cl$. The excess ammonia was evaporated and the residue was diluted with 10% HCl. The acidic solution was extracted with ether. The ether extracts were combined and back washed with brine. The ether solution was dried with $MgSO_4$, then the ether was removed in vacuo. The crude alcohol IX was dissolved in 3 ml of DMF and treated with 100 mg (0.66 mmole) of t-$BuMe_2SiCl$ and ~300 mg of imidazole for 24 hours at room temperature. The reaction mixture was diluted with ether and washed sequentially with saturated $NaHCO_3$, water and brine. The volume of ether was reduced in vacuo to ~20 ml then excess $LiAlH_4$ (~300 mg) was added. The reaction mixture was refluxed for 1 hour then quenched with $Na_2SO_4.H_2O$. The ether was removed in vacuo. The crude spiroketal alkenyl alcohol XI was partially purified using flash chromat. (Hex-:ethyl acetate 20:1, 15:1 etc.). The alcohol XI was then dissolved in 0.5 ml $CH_2Cl_2$ and added to preformed Collins reagent (0.112 ml pyridine-1.45 mmole; 56 mg $CrO_3$-0.56 mmole in 10 ml $CH_2Cl_2$). The reaction mixture was stirred for 35 min then diluted with ether. The ether was washed sequentially as follows: 5% NaOH, $H_2O$ until clear, 10% HCl, saturated $NaHCO_3$ and brine. The solution was dried over $MgSO_4$ and the solvent removed in vacuo. The product was purified by flash chromat. (5%, 10%, etc.-ethyl acetate-hex.) to 9.8 mg (26%) of O-protected spiroketal alkenyl aldehyde XII, wherein $SiR_3$ is t-$BuMe_2Si$.

(B) Synthesis of Southern Hemisphere Intermediate (1) Conversion of XIII to XIV

3-Methyl-4-methoxy benzoic acid XIII (3.5 g, 0.021 mol) was stirred with 9 mL of $SOCl_2$ at 25° for 24 hours. The excess $SOCl_2$ was removed in vacuo and the residue distilled (70°-73°/0.1 mm) to give the acid chloride (3.5 g, 90%), a white solid.

The solid was dissolved in 30 mL of distilled $CH_2Cl_2$ and added to 3.2 g (0.036 mol, 2 eq) of 2-methyl-2-aminopropanol in 15 mL of $CH_2Cl_2$. The mixture was stirred for 2 hours at 25° and then filtered. The filtrate was concentrated in vacuo to give a colorless oil.

Thionyl chloride (15 mL) was slowly added to the oil and the resulting solution stirred at 25° for 30 min. The thionyl chloride was removed in vacuo, dilute HCl (5%/ca. 300 mL) was added to the residue, and the solution washed with ether. The aqueous fraction was basified with 25% NaOH and extracted 3 times with ether. The ether solution was washed with water, brine, dried over $K_2CO_3$ and concentrated. The resulting oil was distilled (95°-100°/0.15 mm) to give a colorless viscous oil which solidified upon cooling (3.45 g, 88% based on acid chloride). Recrystallization from ether-hexane gave white crystals of the aryloxazoline XIV, m.p. 45°-46.5°.

(2) Conversion of XIV to XV

The aryloxazoline XIV (1.63 g, 7.44 mmol) was dissolved in 30 mL of ether and cooled to 0°. s-Butyllithium (1.3 M, 6.8 mL, 8.84 mmol) was added and the mixture stirred at 0° for 4 hours. The contents of the flask were transferred to a second flask containing 0.91 mL of $Ac_2O$ in 10 mL of ether at -78°. This mixture was stirred at -78° for 15 min., then allowed to warm to 25°. Saturated $NH_4Cl$ was added and the mixture extracted with ether. The ether solution was washed with saturated $NaHCO_3$, brine and dried over $MgSO_4$.

The solvent was removed in vacuo and the residue purified by flash chromatography (4:1 hexane-EtOAc). The ortho ketone XV was obtained as a yellow oil, 1.00 g, 51%.

(3) Conversion of XV to XVI

The ortho ketone XV (1.85 g, 7.08 mmol) was dissolved in 35 mL of ether, the solution cooled to 0° and 8.8 mL (9.7 mmol) of 1.1 M vinylmagnesium bromide added. The mixture was stirred at 0° for 15 min., allowed to warm to 25° and then quenched with saturated $NH_4Cl$. The mixture was extracted twice with ether. The ether solution was washed with brine and dried over $MgSO_4$. Removal of solvents in vacuo gave 2.00 g (98%) of an iminolactone as a yellow solid suitable for further use. Recrystallization from ether-hexane afforded a white solid, m.p. 105°-106°.

The iminolactone (0.98 g, 3.39 mmol) was dissolved in 25 mL of THF, 2.5 mL of 3 M $H_2SO_4$ added, and the mixture stirred for 12 hours at 25°. The mixture was poured into water and extracted twice with ether. The ether solution was washed with saturated $NaHCO_3$, brine and dried over $MgSO_4$. Removal of all solvents in vacuo afforded 0.60 g (88%) of the lactone XVI as an off-white solid, suitable for further use. Recrystallization from $CH_2Cl_2$-ether yielded white crystals, m.p. 135°-6°.

(4) Conversion of XVI to XVII to XVIII to XIX to XX

Diphenyl phosphine (1.53 mL, 8.81 mmol) was dissolved in 25 mL of THF under Ar atmosphere and the solution cooled to -22°. n-Butyllithium (1.59 M) was added until a yellow color persisted and then an additional 5.5 mL (8.75 mmol) was added. To the red solution was added the lactone XVI (1.6 g, 7.34 mmol) in 25 mL of THF, the mixture stirred at -22° for 30 min., and allowed to warm to 25° and stirred for 3 hours. Ether saturated with HCl gas was added until the mixture turned wet litmus red, and all solvents were removed in vacuo. The resulting green gel (the aryl alkenyl phosphine XVII) was dissolved in 100 mL of $CHCl_3$, 5 mL of AcOH added and air bubbled through the solution for 12 hours. The $CHCl_3$ was removed in vacuo and the AcOH removed as an azeotrope with heptane. Ethylene glycol (40 mL) and 2 g of sodium hydroxide were added and the mixture was heated at 140° for 12 hours. The brown mixture was poured into water and washed with ether. The aqueous solution was acidified to pH1 with 5% HCl and extracted 4 times with ether. The combined ether fractions were washed with brine, dried over $MgSO_4$ and evaporated. The residue was purified by flash chromatography using hexane-EtOAc-AcOH; 25:10:1, 20:10:1, 15:10:1. Obtained were:

1. The Z acid, 1.31 g, 36% as a pale orange solid
2. The E acid, 1.03 g, 33% as an off-white foam The alkenyl phosphine oxide aryl acids XVIII were converted to their methyl esters XIX by treatment with diazomethane.

Sodium hydride (4.2 mg, 0.106 mmol, 60% oil dispersion) was added to 2 mL of dry THF. The methyl ester XIX (46.1 mg, 0.106 mmol) in 3 mL of THF was added followed by a trace of methanol in THF. The mixture was stirred for 1 hour at 25° to form in the mixture the aryl alkenyl phosphine oxide anion XX, this mixture being suitable for use in the subsequent linking step with the northern hemisphere intermediate XII.

(C) Linking of Northern and Southern Hemisphere Intermediates

To the basic solution mixture containing the aryl alkenyl phosphine oxide anion XX, a trace of KH was added followed by the O-protected spiroketal alkenyl aldehyde XII (31 mg, 0.071 mmol) in 2 mL of THF. The mixture was stirred overnight at 25°, poured into water and extracted 3 times with ether. The ether fraction was washed with brine, dried over $MgSO_4$ and evaporated. Preparative TLC (25:1 hexane-EtOAc) afforded the diene-linked O-protected intermediate XXI (5.0 mg, 11% based on aldehyde), a colorless glass.

The O-protected linked intermediate XXI (2.1 mg, 0.0032 mmol) was dissolved in 2 mL of THF and excess (5 drops) $Bu_4NF$/THF solution added. The orange solution was stirred for 3 hours at 25°. Water was added and the mixture was extracted twice with ether. The ether solution was washed with brine, dried over $MgSO_4$ and evaporated.

The crude deprotected alcohol intermediate XXII was dissolved in 3 mL of THF and added to one drop (excess) of 35% K H/oil dispersion (washed with pentane) in 3 mL of THF. The mixture was stirred at 25° for 3 hours. Water was added and the mixture was extracted twice with ether. The ether solution was washed with brine, dried over $MgSO_4$ and evaporated. Preparative TLC (13: hexane-ether) afforded the cyclized spiroketal macrolide XXIII (1.1 mg, 69%) as a colorless glass.

We claim:
1. A spiroketal having the general formula:

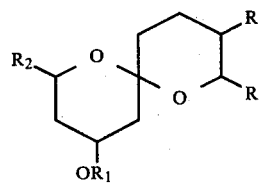

wherein
R is alkyl;
$R_1$ is hydrogen, alkyl, aryl, aralkyl, COR. or $SiR_3$;
$R_2$ is $(CH_2)_xCHO$, $(CH_2)_xCH (OZ')CR=CH_2$, or $(CH_2)_xCH=CRCH_2CHRZ$;
x is 1 to 20
Z is CHO, $CH_2OH$, COOH, or $COSiR_3$; and
Z' is hydrogen or $COCH_2R$.

2. The spiroketal of claim 1 wherein R is a lower alkyl.

3. The spiroketal of claim 1, wherein $R_1$ is benzyl, and $R_2$ is $(CH_2)_xCHO$.

4. The spiroketal of claim 1, wherein $R_1$ is benzyl, and $R_2$ is $(CH_2)_x$—CH (OZ')—CR=$CH_2$.

5. The spiroketal of claim 1, wherein $R_1$ is benzyl or H, and $R_2$ is $(CH_2)_x$—CH=CR—$CH_2$—CHR—$CO_2H$.

6. The spiroketal of claim 1, wherein $R_1$ is $SiR_3$; $R_2$ is $(CH_2)_x$—CH=CR—$CH_2$—CHR—Z; and Z is $CO_2SiR_3$, $CH_2OH$ or CHO.

* * * * *